(12) United States Patent
Alleyne, Jr. et al.

(10) Patent No.: US 9,371,263 B2
(45) Date of Patent: Jun. 21, 2016

(54) PROTECTIVE EFFECTS OF CURCUMIN AGAINST HEMORRHAGIC STROKE INJURY

(71) Applicant: Augusta University Research Institute, Inc., Augusta, GA (US)

(72) Inventors: Cargill H. Alleyne, Jr., Martinez, GA (US); Krishnan M. Dhandapani, Evans, GA (US); Ken Wen, Shanghai (CN); MingLiang Ma, Shanghai (CN); WenJing Hu, Shanghai (CN)

(73) Assignees: Augusta University Research Institute, Inc., Augusta, GA (US); East China Normal University, Shanghai (CN)

( * ) Notice: Subject to any disclaimer, the term of this patent is extended or adjusted under 35 U.S.C. 154(b) by 0 days.

(21) Appl. No.: 14/492,294

(22) Filed: Sep. 22, 2014

(65) Prior Publication Data

US 2015/0087705 A1 Mar. 26, 2015

Related U.S. Application Data

(60) Provisional application No. 61/880,441, filed on Sep. 20, 2013.

(51) Int. Cl.
| | |
|---|---|
| *C07C 49/248* | (2006.01) |
| *C07C 49/235* | (2006.01) |
| *C07C 49/255* | (2006.01) |
| *C07C 59/90* | (2006.01) |
| *C07C 69/738* | (2006.01) |

(52) U.S. Cl.
CPC .............. *C07C 49/248* (2013.01); *C07C 49/235* (2013.01); *C07C 49/255* (2013.01); *C07C 59/90* (2013.01); *C07C 69/738* (2013.01)

(58) Field of Classification Search
CPC .. C07C 49/235; C07C 49/255; C07C 49/248; C07C 59/90; C07C 69/738
See application file for complete search history.

(56) References Cited

U.S. PATENT DOCUMENTS

| | | | | |
|---|---|---|---|---|
| 8,236,852 | B2 * | 8/2012 | Shih et al. | 514/541 |
| 8,841,326 | B2 * | 9/2014 | Vander Jagt | A61K 31/12 514/332 |
| 2008/0033055 | A1 * | 2/2008 | Miller et al. | 514/679 |

OTHER PUBLICATIONS

Nurfina et al, European Journal of Medicinal Chemistry, 1997, 32(4), 321-328.*
Khan et al, Bioorganic Chemistry, 2012, 40, 30-38.*
Anand, et al., "Bioavailability of curcumin: problems and promises", Mol. Pharm., 4:807-18 (2007).
Baum, et al., "Six-month randomized, placebo-controlled, double-blind, pilot clinical trial of curcumin in patients with Alzheimer disease" , J. Clin. Psychopharmacol., 28:110-3 (2008).
Cheng, et al., "Upregulation of Bcl-x and Bfl-1 as a potential mechanism of chemoresistance, which can be overcome by NF-kappaB inhibition" , Oncogene, 19:4936-4940 (2001).
Dhandapani, et al, "Curcumin suppresses growth and chemoresistance of human glioblastoma cells via AP-1 and NFkappaB transcription factors" , J. Neurochem., 102:522-38 (2007).
Lao, et al., "Dose escalation of a curcuminoid formulation" , BMC Complement Altern. Med., 6:10 (2006).
Legler, at al., "Cancer surveillance series [corrected]: brain and other central nervous system cancers: recent trends in incidence and mortality", J. Natl. Cancer Inst,. 91:1382-90 (1999).
Singh, et al., "Identification of human braid tumour initiating cells" , Nature, 432:396-401 (2004).

* cited by examiner

*Primary Examiner* — Shailendra Kumar
(74) *Attorney, Agent, or Firm* — Pabst Patent Group LLP

(57) ABSTRACT

Disclosed herein are compounds, compositions and methods for preventing and treating diseases such as intracerebral hemorrhage, cancer, or conditions associated with damaged cells, activated lymphocytes, or microbial products. The disclosed compounds are curcumin analogs. The curcumin analogs possess anti-inflammatory and antioxidant properties, which in part, reduce AP-1 and NF-κB activity.

15 Claims, 7 Drawing Sheets

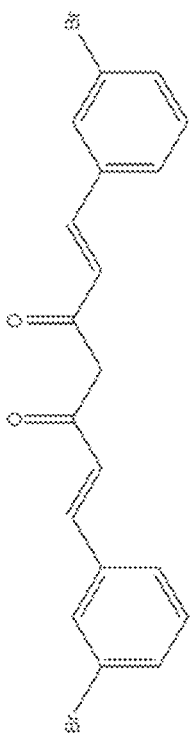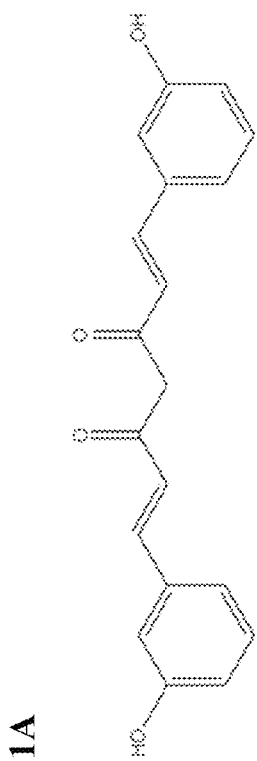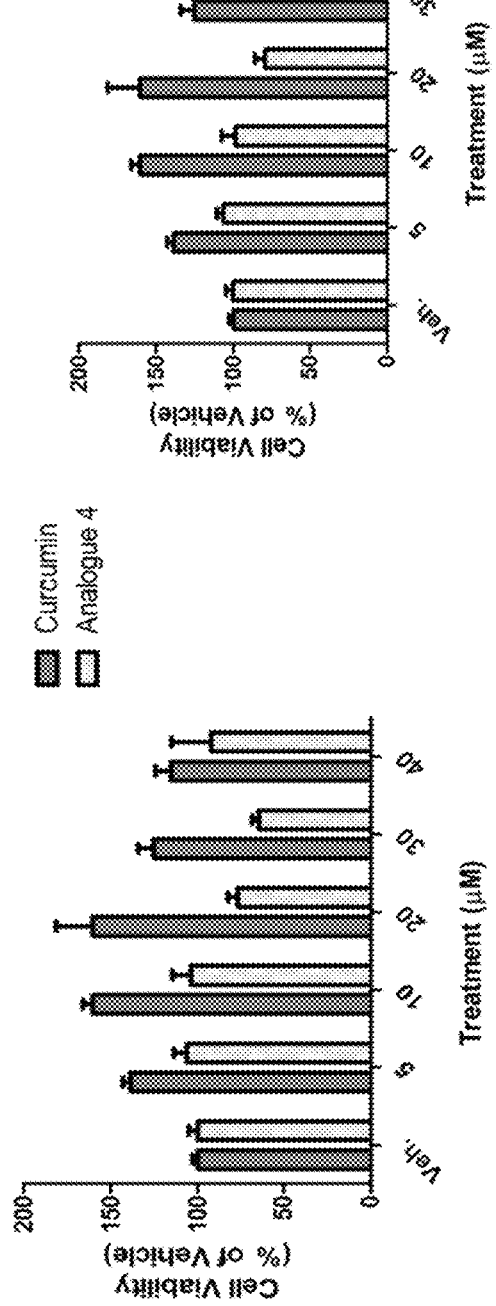
FIGS. 1A & 1B

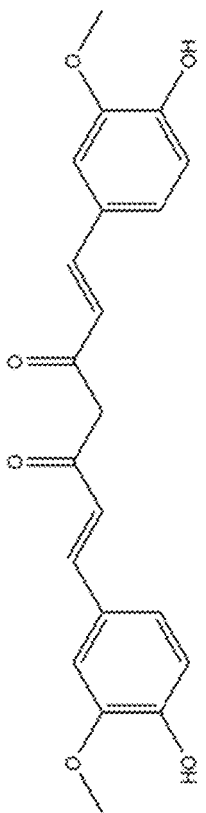
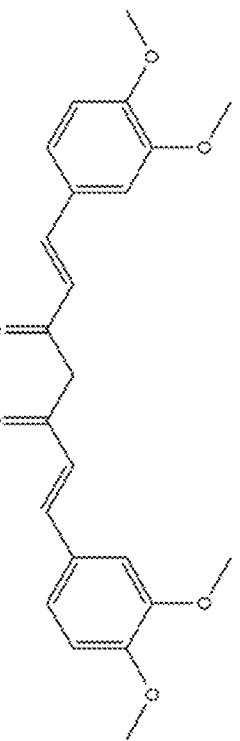
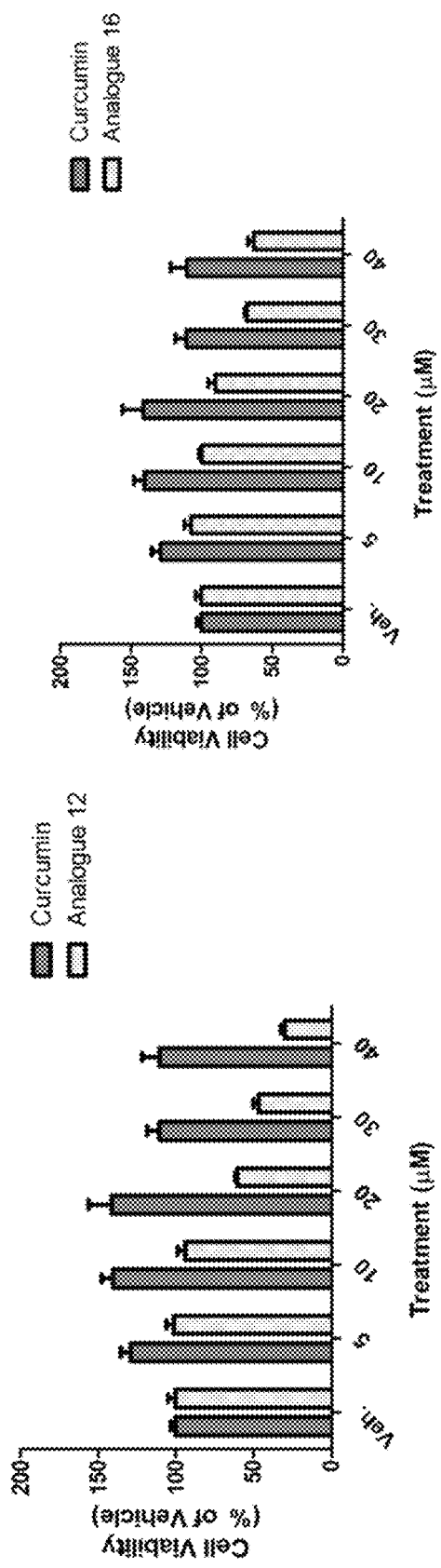
FIGS. 1C & 1D

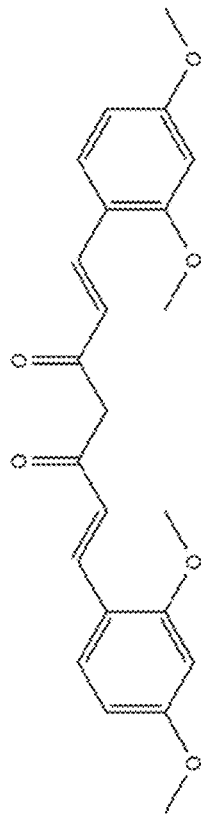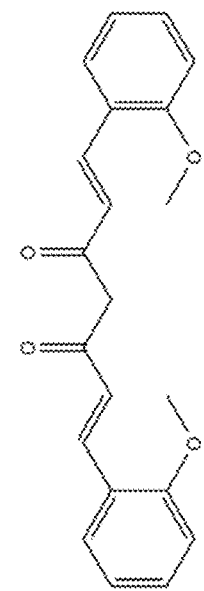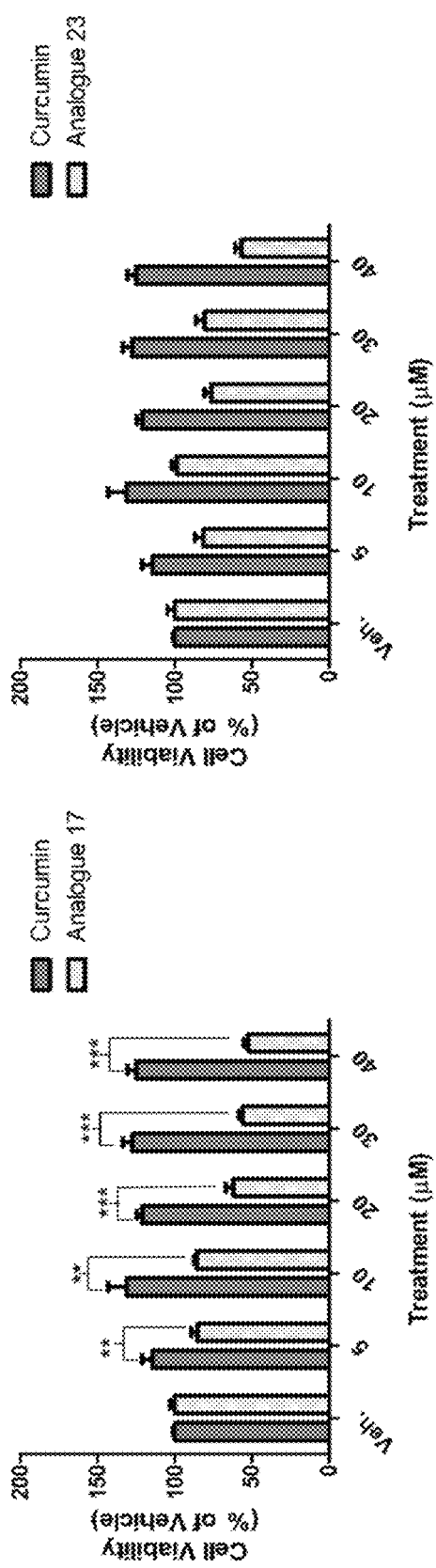
FIGS. 1E & 1F

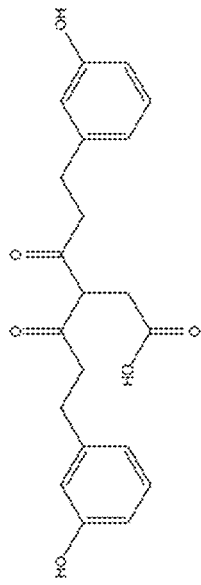
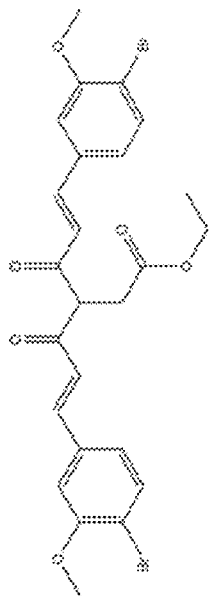
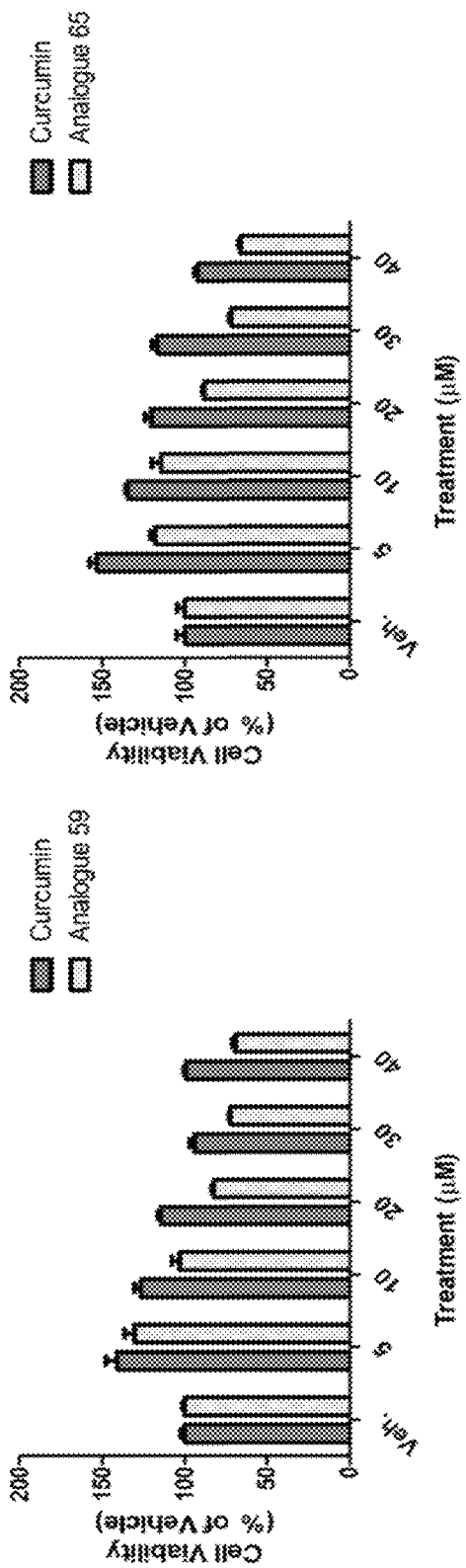
FIGS. 1M & 1N

PROTECTIVE EFFECTS OF CURCUMIN AGAINST HEMORRHAGIC STROKE INJURY

CROSS REFERENCE TO RELATED APPLICATIONS

This application claims benefit to U.S. Ser. No. 61/880,441 filed on Sep. 20, 2013, and which is incorporated by reference in its entirety.

FIELD OF THE INVENTION

This invention generally relates to compounds, compositions, and methods for preventing and treating diseases such as intracerebral hemorrhage, cancer or conditions associated with damaged cells, activated lymphocytes, or microbial products. The compounds are curcumin analogs.

BACKGROUND OF THE INVENTION

Gliomas, the most frequent primary brain tumors in adults, are debilitating malignancies that arise from the transformation of astrocytes or glial precursors (Singh et al., 2004, Nature 432, 396-401). The most common and aggressive form of glioma, glioblastoma multiforme (GBM), is associated with a median survival of less than 12 months with a <6% survival rate following 24 months (Legler et al., 1999, J. Natl. Cancer Inst. 91, 1382-1390). GBM commonly over-express epidermal growth factor receptor and platelet-derived growth factor receptor and contain mutations in the phosphatase and tensin homolog and p53 genes, which contribute to phosphoinositide-3-kinase (PI3K)/Akt and Ras/mitogen-activated protein kinase activation and potentially regulate transcription factors including AP-1 and NFκB.

Intracerebral hemorrhage (ICH) induces 50-60% mortality within the first year and is associated with long-term disability in many survivors. Primary ICH may be caused by the rupture of small vessels damaged by chronic hypertension or amyloid angiopathy. This can lead to the accumulation of erythrocytes within the parenchyma and the formation of a space-occupying hematoma. Hematoma volume directly correlates with neurological outcome, supporting clot evacuation as a strategy to attenuate brain injury and improve patient prognosis. Unfortunately, a limited number of suitable surgical candidates and/or unfavorable size/location of the mass lesion may restrict the utility of neurosurgical intervention. As such, treatment options remain largely supportive, reinforcing the notion that ICH is the least treatable form of stroke and stressing the need for novel therapeutic approaches. Studies have shown early phase predictive markers of acute hematoma growth include an inflammatory reaction and neurological deterioration in ICH patients. The activation of the pro-inflammatory transcription factor, NFκB, increased the expression of inflammatory mediators associated with cell death, increased blood-brain barrier (BBB) permeability, and induced the development of vasogenic edema in ICH subjects. Thus, a reduction in inflammatory activation may limit neurovascular injury and improve clinical outcomes following ICH.

Curcumin (diferuloylmethane), a naturally occurring polyphenol derived from the root of the rhizome, Curcuma longa, possesses anti-inflammatory and antioxidant properties, in part via a reduction in AP-1 and NFκB activity. Curcumin recently entered Phase I clinical trials for the treatment of several high-risk cancers (Cheng et al., 2001, Oncogene, 19, 4936-4940), and a recent study shows curcumin may exert multiple beneficial effects in glioma cells, including inhibition of cellular growth, invasion, and angiogenesis (Dhandapani et al., 2007, J. Neurochem., 102, 522-538).

Curcumin has been safely consumed by humans for centuries, including use as an anti-inflammatory agent in Ayurveda, an ancient Indian system of medicine. Recent clinical trials also demonstrated that oral administration of curcumin resulted in bioactivity with minimal adverse effects, even when administered at high doses. However, clinical trials in humans have indicated that the systemic bioavailability of orally administered curcumin is relatively low (Anand et al., Mol. Pharm., 2007, 4, 807-818) and that mostly metabolites of curcumin, instead of curcumin itself, are detected in plasma or serum following oral consumption (Baum et al., J. Clin. Psychopharmacol., 2008, 28, 110-113; Lao et al., BMC Complement Altern. Med., 2006, 6, 10). In the intestine and liver, curcumin is readily conjugated to form curcumin glucuronides and curcumin sulfates or, alternately, reduced to hexahydrocurcumin.

It is an object of this invention to provide compounds and compositions that have greater systemic bioavailability than curcumin.

It is another object of this invention to provide compounds, compositions and methods that treat intracerebral hemorrhage.

It is another object of this invention to compounds, compositions and methods that prevent and treat malignant gliomas.

It is also another object of the present invention to provide compounds, compositions and methods for the treatment of diseases or conditions associated with NFκB activity.

SUMMARY OF THE INVENTION

Disclosed herein are compounds, compositions and methods for preventing and treating diseases such as intracerebral hemorrhage, cancer, or conditions associated with damaged cells, activated lymphocytes, or microbial products. The compounds are curcumin analogs.

In some forms, the compounds, compositions and methods relate to the formula I, or a pharmaceutically acceptable salt, prodrug, clathrate, tautomer or solvate thereof, wherein:

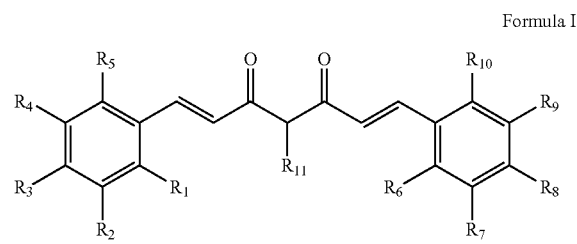

Formula I $R_1$, $R_2$, $R_3$, $R_4$, $R_5$, $R_6$, $R_7$, $R_8$, $R_9$ and $R_{10}$ are independently selected from the group consisting of hydrogen, alkyl, halogen, alkoxy, amino, alkylamino, dialkylamino, cyano, nitro, formyl, carboxyl, alkoxycarbonyl, alkoxydialkylamino, aminocarbonyl, alkylaminocarbonyl, dialkylamino carbonyl, haloalkyl, haloalkloxy, haloalkylamino, and di(haloalkyl)amino, and $R_{11}$ is selected from the group consisting of hydrogen, alkyl, halogen, alkoxy, amino, alkylamino, dialkylamino, carboxyl, alkoxycarbonyl, ester, alkyl ester, haloalkyl, haloalkloxy, haloalkylamino, and di(haloalkyl)amino.

DETAILED DESCRIPTION OF THE INVENTION

I. Definitions

Figures 1G, 1H:
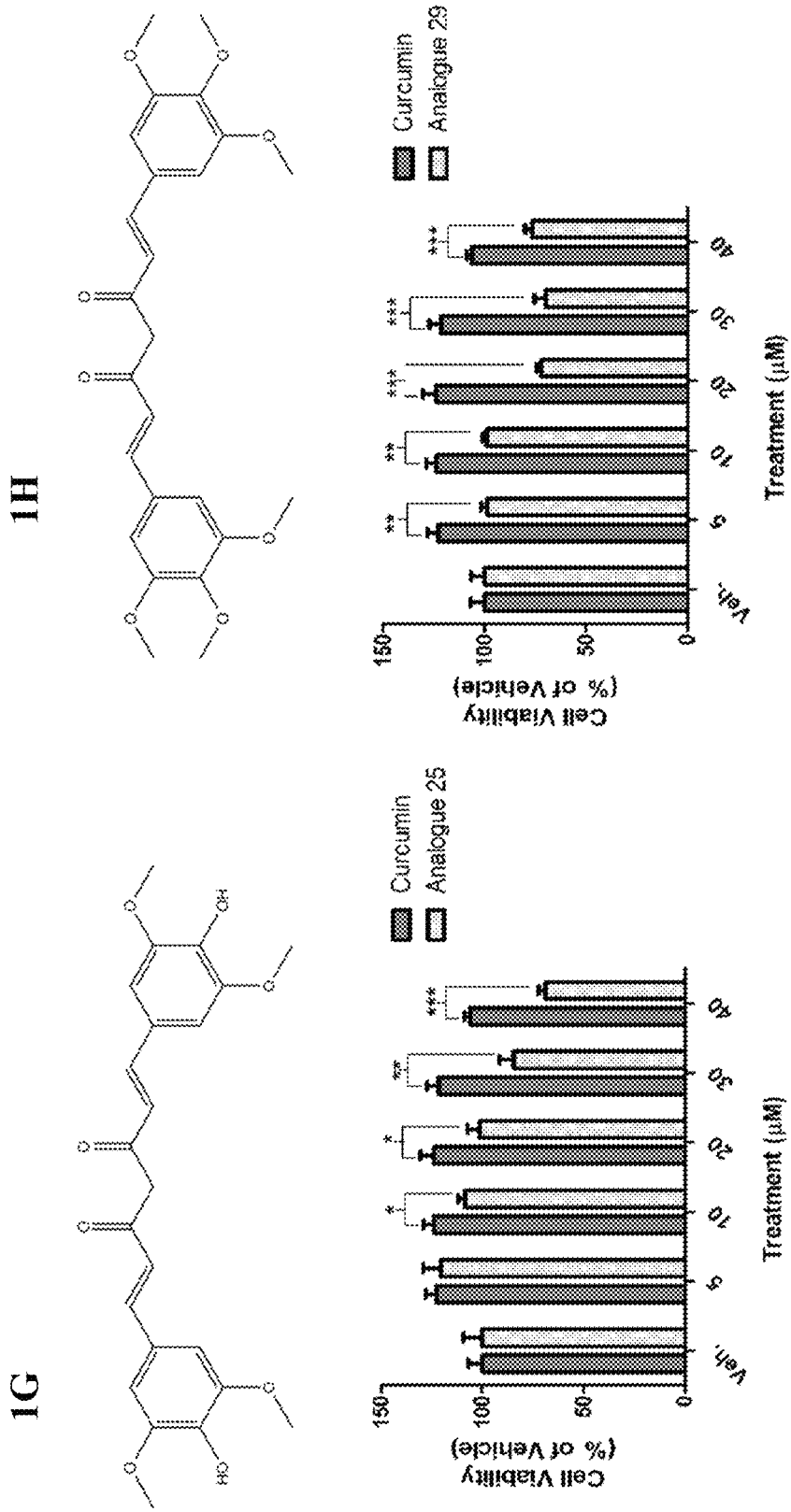
FIGS. 1A to 1N are bar graphs showing the effects of curcumin (grey bar) and curcumin analogues (white bar) on glioma cells viability.
Figures 1I, 1J:
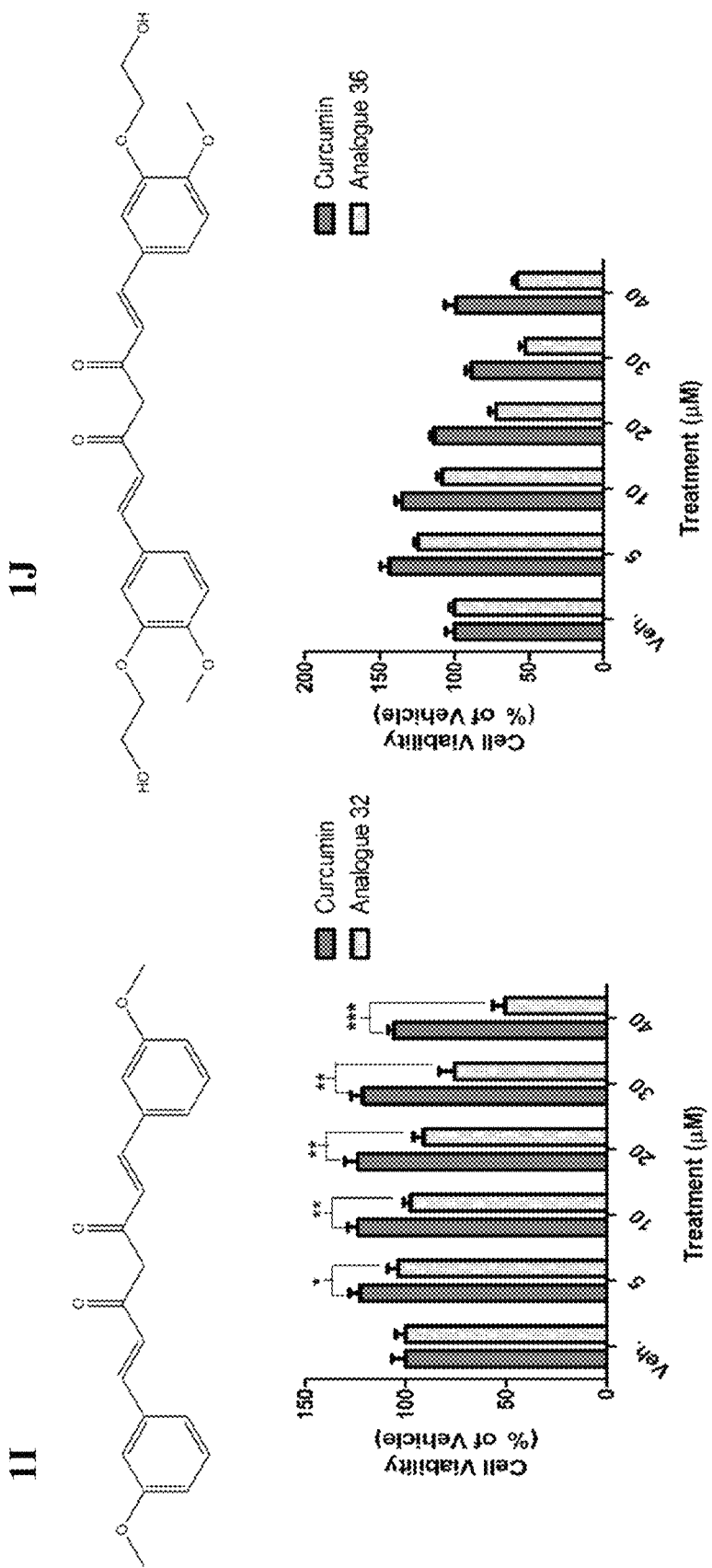
Figures 1K, 1L:

As used in the specification and the appended claims, the singular forms "a," "an" and "the" include plural referents unless the context clearly dictates otherwise. Thus, for example, reference to "a curcumin analog" refers to one or mixtures of curcumin analogs, and references to "the method of treatment" includes reference to equivalent steps and methods known to those skilled in the art, and so forth.

The term "cell" as used herein also refers to individual cells, cell lines, or cultures derived from such cells. A "culture" refers to a composition including isolated cells of the same or a different type. The term co-culture is used to designate when more than one type of cell are cultured together in the same dish with either full or partial contact with each other.

"Optional" or "optionally" means that the subsequently described event or circumstance may or may not occur, and that the description includes instances where said event or circumstance occurs and instances where it does not.

By "prevent" or other forms of prevent means to stop a particular characteristic or condition. Prevent does not require comparison to a control as it is typically more absolute than, for example, reduce or inhibit. As used herein, something could be reduced but not inhibited or prevented, but something that is reduced could also be inhibited or prevented. It is understood that where reduce, inhibit or prevent are used, unless specifically indicated otherwise, the use of the other two words is also expressly disclosed. Thus, if inhibits phosphorylation is disclosed, then reduces and prevents phosphorylation are also disclosed.

By "reduce" or other forms of reduce means lowering of an event or characteristic. It is understood that this is typically in relation to some standard or expected value, in other words it is relative, but that it is not always necessary for the standard or relative value to be referred to. For example, "reduces phosphorylation" means lowering the amount of phosphorylation that takes place relative to a standard or a control.

As used throughout, by a "subject" is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human. The subject can also be a non-human.

The term "metabolite" refers to active derivatives produced upon introduction of a compound into a biological milieu, such as a patient.

The term "pro-drug or prodrug" is intended to encompass compounds which, under physiologic conditions, are converted into therapeutically active agents. A common method for making a prodrug is to include selected moieties which are hydrolyzed under physiologic conditions to reveal the desired molecule. In other embodiments, the prodrug is converted by an enzymatic activity of the host animal.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data are provided in a number of different formats, and that this data, represents endpoints and starting points, and ranges for any combination of the data points. For example, if a particular datum point "10" and a particular datum point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

The term "therapeutically effective" means that the amount of the composition used is of sufficient quantity to ameliorate one or more causes or symptoms of a disease or disorder. Such amelioration only requires a reduction or alteration, not necessarily elimination. The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "alkyl" as used herein is a branched or unbranched saturated hydrocarbon moiety. "Unbranched" or "Branched" alkyls include a non-cyclic, saturated, straight or branched chain hydrocarbon moiety having from 1 to 24 carbons, 1 to 12, carbons, 1 to 6 carbons, or 1 to 4 carbon atoms. Examples of such alkyl radicals include methyl, ethyl, propyl, butyl, pentyl, hexyl, heptyl, octyl, n-propyl, iso-propyl, butyl, n-butyl, sec-butyl, t-butyl, amyl, t-amyl, n-pentyl and the like. Lower alkyls include a noncyclic, saturated, straight or branched chain hydrocarbon residue having from 1 to 4 carbon atoms, i.e., $C_1$-$C_4$ alkyl.

Moreover, the term "alkyl" as used throughout the specification and claims is intended to include both "unsubstituted alkyls" and "substituted alkyls", the later denotes an alkyl radical analogous to the above definition that is further substituted with one, two, or more additional organic or inorganic substituent groups. Suitable substituent groups include but are not limited to hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido,acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkoxy, heteroaryl, substituted heteroaryl, aryl or substituted aryl. It will be understood by those skilled in the art that an "alkoxy" can be a substituted of a carbonyl substituted "alkyl" forming an ester. When more than one substituent group is present then they can be the same or different. The organic substituent moieties can include from 1 to 12 carbon atoms, or from 1 to 6 carbon atoms, or from 1 to 4 carbon atoms. It will be understood by those skilled in the art that the moieties substituted on the "alkyl" chain can themselves be substituted, as described above, if appropriate.

The term "alkenyl" as used herein is an alkyl residue as defined above that also includes at least one carbon-carbon double bond in the backbone of the hydrocarbon chain. Examples include but are not limited to vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2-heptenyl, 3-heptenyl, 4-heptenyl, 5-heptenyl, 6-heptenyl and the like. The term "alkenyl" includes dienes and trienes of straight and branch chains.

The term "alkynyl" as used herein is an alkyl residue as defined above that includes at least one carbon-carbon triple bond in the backbone of the hydrocarbon chain. Examples include but are not limited ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "cycloalkyl" as used herein is a saturated hydrocarbon structure wherein the structure is closed to form at least one ring. Cycloalkyls typically include a cyclic radical containing 3 to 8 ring carbons, such as cyclopropyl, cyclobutyl, cyclopentyl, cyclopenyl, cyclohexyl, cycloheptyl and the like. Cycloalkyl radicals can be multicyclic and can contain a total of 3 to 18 carbons, or preferably 4 to 12 carbons, or 5 to 8 carbons. Examples of multicyclic cycloalkyls include decahydronapthyl, adamantyl, and like radicals.

Moreover, the term "cycloalkyl" as used throughout the specification and claims is intended to include both "unsubstituted cycloalkyls" and "substituted cycloalkyls", the later denotes an cycloalkyl radical analogous to the above definition that is further substituted with one, two, or more additional organic or inorganic substituent groups that can include but are not limited to hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido,acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkoxy, heteroaryl, substituted heteroaryl, aryl or substituted aryl. When the cycloalkyl is substituted with more than one substituent group, they can be the same or different. The organic substituent groups can include from 1 to 12 carbon atoms, or from 1 to 6 carbon atoms, or from 1 to 4 carbon atoms.

The term "cycloalkenyl" as used herein is a cycloalkyl radical as defined above that includes at least one carbon-carbon double bond. Examples include but are not limited to cyclopropenyl, 1-cyclobutenyl, 2-cyclobutenyl, 1-cyclopentenyl, 2-cyclopentenyl, 3-cyclopentenyl, 1-cyclohexyl, 2-cyclohexyl, 3-cyclohexyl and the like.

The term "alkoxy" as used herein is an alkyl residue, as defined above, bonded directly to an oxygen atom, which is then bonded to another moiety. Examples include methoxy, ethoxy, n-propoxy, iso-propoxy, n-butoxy, t-butoxy, iso-butoxy and the like.

The term "mono-substituted amino" as used herein is a moiety including an NH radical substituted with one organic substituent group, which include but are not limited to alkyls, substituted alkyls, cycloalkyls, aryls, or arylalkyls. Examples of mono-substituted amino groups include methylamino (—NH—$CH_3$); ethylamino (—NH$CH_2CH_3$), hydroxyethylamino (—NH—$CH_2CH_2OH$), and the like.

The term "di-substituted amino" as used herein is a moiety including a nitrogen atom substituted with two organic radicals that can be the same or different, which can be selected from but are not limited to aryl, substituted aryl, alkyl, substituted alkyl or arylalkyl, wherein the terms have the same definitions found throughout. Some examples include dimethylamino, methylethylamino, diethylamino and the like.

The term "haloalkyl" as used herein an alkyl residue as defined above, substituted with one or more halogens, preferably fluorine, such as a trifluoromethyl, pentafluoroethyl and the like.

The term "haloalkoxy" as used herein a haloalkyl residue as defined above that is directly attached to an oxygen to form trifluoromethoxy, pentafluoroethoxy and the like.

The term "aryl" as used herein is a ring radical containing 6 to 18 carbons, or preferably 6 to 12 carbons, including at least one aromatic residue therein. Examples of such aryl radicals include phenyl, naphthyl, and ischroman radicals. Moreover, the term "aryl" as used throughout the specification and claims is intended to include both "unsubstituted aryls" and "substituted aryls", the later denotes an aryl ring radical as defined above that is substituted with one or more, preferably 1, 2, or 3 organic or inorganic substituent groups, which include but are not limited to a halogen, alkyl, alkenyl, alkynyl, hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy or haloalkoxy, aryl, substituted aryl, heteroaryl, heterocyclic ring, ring wherein the terms are defined herein. The organic substituent groups can include from 1 to 12 carbon atoms, or from 1 to 6 carbon atoms, or from 1 to 4 carbon atoms. It will be understood by those skilled in the art that the moieties substituted on the "aryl" can themselves be substituted, as described above, if appropriate.

The term "heteroaryl" as used herein is an aryl ring radical as defined above, wherein at least one of the ring carbons, or preferably 1, 2, or 3 carbons of the aryl aromatic ring has been replaced with a heteroatom, which include but are not limited to nitrogen, oxygen, and sulfur atoms. Examples of heteroaryl residues include pyridyl, bipyridyl, furanyl, and thiofuranyl residues. Substituted "heteroaryl" residues can have one or more organic or inorganic substituent groups, or preferably 1, 2, or 3 such groups, as referred to herein-above for aryl groups, bound to the carbon atoms of the heteroaromatic rings. The organic substituent groups can include from 1 to 12 carbon atoms, or from 1 to 6 carbon atoms, or from 1 to 4 carbon atoms.

The term "heterocyclyl" or "heterocyclic group" as used herein is a non-aromatic mono- or multi ring radical structure having 3 to 16 members, preferably 4 to 10 members, in which at least one ring structure include 1 to 4 heteroatoms (e.g., O, N, S, P, and the like). Heterocyclyl groups include, for example, pyrrolidine, oxolane, thiolane, imidazole, oxazole, piperidine, piperizine, morpholine, lactones, lactams, such as azetidiones, and pyrrolidiones, sultams, sultones, and the like. Moreover, the term "heterocyclyl" as used throughout the specification and claims is intended to include both "unsubstituted alkyls" and "substituted alkyls", the later denotes an aryl ring radical as defined above that is substituted with one or more, preferably 1, 2, or 3 organic or inorganic substituent groups, which include but are not limited to a halogen, alkyl, alkenyl, alkynyl, hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy or haloalkoxy, aryl, substituted aryl, heteroaryl, heterocyclic ring, ring wherein the terms are defined herein. The organic substituent groups can include from 1 to 12 carbon atoms, or from 1 to 6 carbon atoms, or from 1 to 4 carbon atoms. It will be understood by those skilled in the art that the moieties substituted on the "heterocyclyl" can themselves be substituted, as described above, if appropriate.

The term "halo" or "halogen" refers to a fluoro, chloro, bromo or iodo group.

For the purposes of the present disclosure the terms "compound," "analog," and "composition of matter" stand equally well for the chemical entities described herein, including all enantiomeric forms, diastereomeric forms, salts, and the like, and the terms "compound," "analog," and "composition of matter" are used interchangeably throughout the present specification.

The term "ester" as used herein is represented by the formula —C(O)OA, where A can be an alkyl, halogenated alkyl, alkenyl, alkynyl, aryl, heteroaryl, cycloalkyl, cycloalkenyl, heterocycloalkyl, or heterocycloalkenyl group described above.

The term "carbonyl group" as used herein is represented by the formula C=O.

The term "ether" as used herein is represented by the formula AOAl, where A and Al can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "alkoxy" as used herein is an alkyl group bound through a single, terminal ether linkage; that is, an "alkoxy" group may be defined as —OR where R is alkyl as defined above. A "lower alkoxy" group is an alkoxy group containing from one to six carbon atoms.

The term "aralkyl" as used herein is an aryl group having an alkyl, alkynyl, or alkenyl group as defined above attached to the aromatic group. An example of an aralkyl group is a benzyl group.

The term "hydroxyalkyl group" as used herein is an alkyl, alkenyl, alkynyl, aryl, aralkyl, cycloalkyl, halogenated alkyl, or heterocycloalkyl group described above that has at least one hydrogen atom substituted with a hydroxyl group.

The term "alkoxyalkyl group" is defined as an alkyl, alkenyl, alkynyl, aryl, aralkyl, cycloalkyl, halogenated alkyl, or heterocycloalkyl group described above that has at least one hydrogen atom substituted with an alkoxy group described above.

The term "carbonate group" as used herein is represented by the formula —OC(O)OR, where R can be hydrogen, an alkyl, alkenyl, alkynyl, aryl, aralkyl, cycloalkyl, halogenated alkyl, or heterocycloalkyl group described above.

$R_1$, $R_2$, $R_3$, $R_4$, $R_5$, $R_6$, $R_7$, $R_8$, $R_9$ and $R_{10}$ can, independently, possess two or more of the groups listed above. For example, if $R_1$, $R_2$, $R_3$, $R_4$, $R_5$, $R_6$, $R_7$, $R_8$, $R_9$ or $R_{10}$ is a straight chain alkyl group, one of the hydrogen atoms of the alkyl group can be substituted with a hydroxyl group, an alkoxy group, etc. Depending upon the groups that are selected, a first group can be incorporated within second group or, alternatively, the first group can be pendant (i.e., attached) to the second group. For example, with the phrase "an alkyl group including an ester group," the ester group can be incorporated within the backbone of the alkyl group. Alternatively, the ester can be attached to the backbone of the alkyl group. The nature of the group(s) that is (are) selected will determine if the first group is embedded or attached to the second group.

As used herein, the term "activity" refers to a biological activity.

II. Compounds

The compounds disclosed herein are curcumin analogs, or a pharmaceutically acceptable salt, prodrug, clathrate, tautomer or solvate thereof. The compound has the structure:

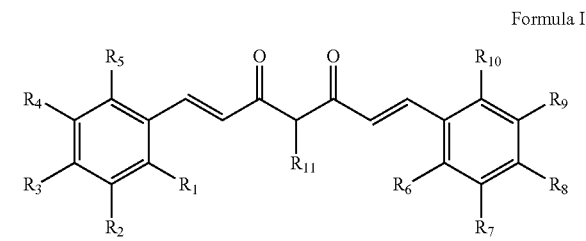

Formula I wherein $R_1$, $R_2$, $R_3$, $R_4$, $R_5$, $R_6$, $R_7$, $R_8$, $R_9$ and $R_{10}$ are independently selected from the group, but are not limited to hydrogen, alkyl, halogen, alkoxy, amino, alkylamino, dialkylamino, cyano, nitro, formyl, carboxyl, alkoxycarbonyl, alkoxydialkylamino, aminocarbonyl, alkylaminocarbonyl, dialkylamino carbonyl, haloalkyl, haloalkloxy, haloalkylamino, and di(haloalkyl)amino, and $R_{11}$ is selected from the group, but is not limited to hydrogen, alkyl, halogen, alkoxy, amino, alkylamino, dialkylamino, carboxyl, alkoxycarbonyl, ester, alkyl ester, haloalkyl, haloalkloxy, haloalkylamino, and di(haloalkyl)amino.

In some forms, $R_1$, $R_2$, $R_3$, $R_4$, $R_5$, $R_6$, $R_7$, $R_8$, $R_9$, and $R_{10}$ can independently be hydrogen, alkyl, halogen, alkoxy, carboxyl, alkoxycarbonyl, haloalkyl, haloalkloxy, and haloalkylamino, and $R_{11}$ can be hydrogen, alkyl, halogen, alkoxy, carboxyl, alkoxycarbonyl, ester, and alkyl ester.

In some forms, $R_1$, $R_2$, $R_3$, $R_4$, $R_5$, $R_6$, $R_7$, $R_8$, $R_9$ and $R_{10}$ can independently be hydrogen, alkyl, halogen, and $C_1$-$C_4$ alkoxy, and $R_{11}$ can be hydrogen, alkyl, alkoxy, carboxyl, alkoxycarbonyl, ester, and alkyl ester.

In some forms, the compound can be:

The compounds disclosed herein also encompass pharmaceutically acceptable salts, esters, and amides of such compounds. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. Pharmaceutically acceptable salts are also prepared by treating the free base with an appropriate amount of a pharmaceutically acceptable acid. Representative phar-

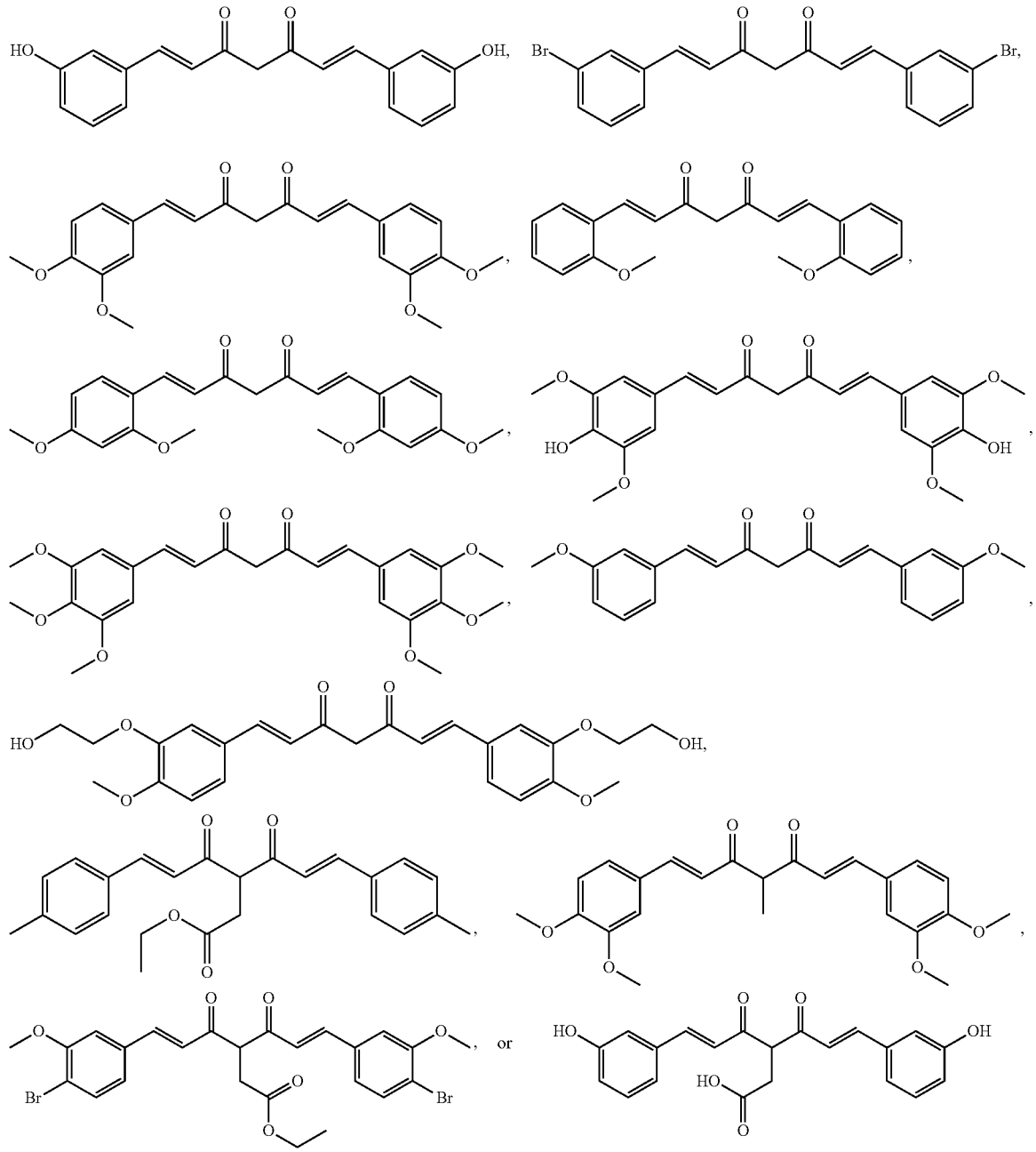

maceutically acceptable acids are inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid. In one aspect, the reaction is conducted in water, alone or in combination with an inert, water-miscible organic solvent, at a temperature of from about 0° C. to about 100° C., such as at room temperature. The molar ratio of the disclosed compounds to base used is chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds and accordingly can serve as prodrugs. Generally, these derivatives will be lower alkyl esters such as methyl, ethyl, and the like. Amide derivatives —(CO)NH$_2$, —(CO)NHR and —(CO)NR$_2$, where R is an alkyl group defined above, can be prepared by reaction of the carboxylic acid-containing compound with ammonia or a substituted amine.

II. Compositions

The curcumin analogs (also referred to herein as "active compounds") can be incorporated into pharmaceutical compositions suitable for administration. Generally, the nature of the analog and the route of administration will influence the choice of composition. Compositions can be formulated for enteral, parenteral, topical, intradermal, subcutaneous or pulmonary administration. Such compositions typically include a pharmaceutically effective amount of a curcumin analog and a pharmaceutically acceptable carrier. See, e.g., *Remington's Pharmaceutical Sciences*, latest edition, by E. W. Martin Mack Pub. Co., Easton, Pa., which discloses typical carriers and conventional methods of preparing pharmaceutical compositions that can be used in conjunction with the preparation of formulations of the compounds described herein and which is incorporated by reference herein.

The pharmaceutical compositions described herein can include, but are not limited to, carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like. These most typically would be standard carriers for administration of compositions to humans. In one aspect, solutions such as sterile water, saline, and buffered solutions at physiological pH can be used. Other compounds will be administered according to standard procedures used by those skilled in the art.

The dosages or amounts of the curcumin analogs described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

1. Compositions for Parenteral Administration

In a preferred embodiment, the disclosed compositions are administered in an aqueous solution, by parenteral injection.

The compositions may also be in the form of a suspension or emulsion. In general, pharmaceutical compositions are provided including effective amounts of a curcumin analog, and optionally include pharmaceutically acceptable diluents, preservatives, solubilizers, emulsifiers, adjuvants and/or carriers. Such compositions include sterile water, buffered saline (e.g., Tris-HCl, acetate, phosphate), pH and ionic strength; and optionally, additives such as detergents and solubilizing agents (e.g., TWEEN® 20, TWEEN 80, Polysorbate 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The compositions may be lyophilized and redissolved/resuspended immediately before use. The formulation may be sterilized by, for example, filtration through a bacteria retaining filter, by incorporating sterilizing agents into the compositions, by irradiating the compositions, or by heating the compositions. Preservatives and other additives can also be present such as, for example, antimicrobials, anti-oxidants, chelating agents, and inert gases and the like. pH can be adjusted with acids or bases, such as hydrochloric acid or sodium hydroxide. The parenteral preparation can be enclosed in ampoules, disposable syringes or multiple dose vials made of glass or plastic.

2. Controlled Delivery Polymeric Matrices

Compositions containing one or more curcumin analog can be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the active agent is dispersed within a solid polymeric matrix or microcapsules, where the core is of a different material than the polymeric shell, and the active agent is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel. The matrix can also be incorporated into or onto a medical device to modulate an immune response, to prevent infection in an immune-compromised patient (such as an elderly person in which a catheter has been inserted or a premature child) or to aid in healing, as in the case of a matrix used to facilitate healing of pressure sores, decubitis ulcers, etc.

Either non-biodegradable or biodegradable matrices can be used for delivery of the curcumin analog, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release,* 5:13-22 (1987); Mathiowitz, et al., *Reactive Polymers,* 6:275-283 (1987); and Mathiowitz, et al., *J. Appl. Polymer Sci.,* 35:755-774 (1988).

The curcumin analog can be incorporated into an inert matrix which permits release by either diffusion or leaching mechanisms, e.g., films or gums. Slowly disintegrating matrices may also be incorporated into the formulation. Another form of a controlled release is one in which the drug is enclosed in a semipermeable membrane which allows water to enter and push drug out through a single small opening due to osmotic effects. For oral formulations, the location of release may be the stomach, the small intestine (the duodenum, the jejunem, or the ileum), or the large intestine. Preferably, the release will avoid the deleterious effects of the stomach environment, either by protection of the active agent (or derivative) or by release of the active agent beyond the stomach environment, such as in the intestine. To ensure full gastric resistance an enteric coating (i.e., impermeable to at least pH 5.0) is essential. These coatings may be used as mixed films or as capsules such as those available from Banner Pharmacaps.

3. Compositions for Oral Administration

Curcumin analogs can also be formulated for oral delivery. Oral solid dosage forms are known to those skilled in the art. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the present proteins and derivatives. See, e.g., Remington's Pharmaceutical Sciences, 21st Ed. (2005, Lippincott, Williams & Wilins, Baltimore, Md. 21201) pages 889-964. The compositions may be prepared in liquid form, or may be in dried powder (e.g., lyophilized) form. Liposomal or polymeric encapsulation may be used to formulate the compositions. See also Marshall, K. In: Modern Pharmaceutics Edited by G. S. Banker and C. T. Rhodes Chapter 10, 1979.

Liquid dosage forms for oral administration, including pharmaceutically acceptable emulsions, solutions, suspensions, and syrups, may contain other components including inert diluents; adjuvants such as wetting agents, emulsifying and suspending agents; and sweetening, flavoring, and perfuming agents.

4. Formulations for Topical Administration

Compositions for topical administration may include ointments, lotions, creams, gels, drops, suppositories, sprays, liquids and powders. Conventional pharmaceutical carriers, aqueous, powder or oily bases, thickeners and the like may be necessary or desirable. The curcumin analogs, and optionally a delivery vehicle, or a combination thereof can be applied topically. Topical administration can include application to the lungs, nasal, oral (sublingual, buccal), vaginal, or rectal mucosa. Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acorn® II nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.). Nektar, Alkermes and Mannkind all have inhalable insulin powder preparations approved or in clinical trials where the technology could be applied to the formulations described herein.

Compositions for administration to the mucosa will typically be spray dried drug particles, which may be incorporated into a tablet, gel, capsule, suspension or emulsion. Standard pharmaceutical excipients are available from any formulator.

5. Effective Amounts

In some in vivo approaches, the compositions are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect.

In some embodiments, the amount of composition administered to the subject is typically effective to reduce the expression of proinflammatory mediators, tumor necrosis factor-a, interleukin-6, and interleukin-1β. In some embodiments, the amount is effective to reduce disruption of the blood-brain barrier, which attenuates the formation of vasogenic edema following intracerebral hemorrhage (ICH). In some embodiments, the amount is effective to increase neurological outcome scores after ICH.

In some embodiments, the amount is effective to activate the production of macrophages. In some embodiments, the amount is effective to activate the production of M2 phenotype macrophages. In some embodiments, the amount is effective to induce the production of M2 phenotype macrophages from M1 phenotype. Typically, the pool of M1 macrophages is decreased.

In some embodiments, the amount is effective to reduce NF-κB activity. In some embodiments, the amount is effective to reduce AP-1 activity. In some embodiments, the amount is effective to prevent and/or treat cancer. In some embodiments, the amount is effective to treat or prevent prostate cancer, glioma, colon cancer, leukemia, non-small cell lung cancer, melanoma, CNS cancer, ovarian cancer, renal cancer, or breast cancer. In some embodiments, the cancer is a malignant glioma. In one embodiment, the glioma is glioblastoma multiforme.

In some embodiments, the amount is effective to induce, augment, or enhance an immune response against a disease or condition associated with microbial products, damaged cells, or activated lymphocytes. In some embodiments, the amount is effective to treat or prevent atherosclerotic plaque, a fibrotic condition, inflammation, sarcoidosis, or multiple sclerosis. In some embodiments, the amount is effective to treat or prevent pulmonary fibrosis or systematic sclerosis. In some embodiments, the amount is effective to promote tissue regeneration. In some embodiments, the amount is effective to promote wound healing, tissue remodeling, angiogenesis, and extracellular matrix (ECM) deposition. In some embodiments, the amount is effective to promote parasite containment. In some embodiments, the amount is effective to produce high levels of anti-inflammatory cytokines, such as IL-10, transforming growth factor (TGF)-β, and low levels of pro-inflammatory cytokines The precise dosage will vary according to a variety of factors such as subject-dependent variables (e.g., age, immune system health, etc.), the disease, and the treatment being effected. As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower. It is believed, however, that the dosage for reducing treating gliomas, ICH, and to induce, augment, or enhance an immune response can be lower than the dosages that are typically administered in the art for treatment of these diseases or infections.

III. Methods

A. Diseases to Be Treated

The disclosed curcumin analogs have a wide variety of uses. The analogs possess anti-inflammatory and antioxidant properties, which in part, reduces AP-1 and NFκB activity. Early-phase predictive markers of acute hematoma growth have been correlated with an inflammatory reaction and with neurological deterioration in patients suffering from ICH. The activation of the proinflammatory transcription factor NF-kB increases the expression of inflammatory mediators associated with cell death, increased BBB edema permeability, and induces the development of vasogenic edema.

GBM commonly over-express epidermal growth factor receptor and platelet-derived growth factor receptor and contain mutations in the phosphatase and tensin homolog and p53 genes, which contribute to phosphoinositide-3-kinase (PI3K)/Akt and Ras/mitogen-activated protein kinase activation and potentially regulate transcription factors including AP-1 and NFκB.

The NF-kB signaling pathway is involved in the activation of macrophages. Macrophages are white blood cells produced by the division of monocytes. Unique stimuli endow macrophages with distinct molecular phenotypes and effector functions. Activating macrophages in the presence of cytokines such as interleukin-4 (IL-4) or IL-13 promotes an "alternatively activated" M2 phenotype. M2 macrophages promote angiogenesis and matrix remodeling while suppressing destructive immunity.

M2 macrophages exhibit potent anti-inflammatory activity and have important roles in wound healing and fibrosis. M2 macrophages produce high levels of fibronectin and a matrix-associated protein, βIG-H3, and they promote fibrogenesis from fibroblastoid cells. The induction of arginase in these cells may lead to polyamine and proline biosynthesis, promoting cell growth, collagen formation, and tissue repair. Thus, alternatively activated macrophages are critically involved in wound healing and tissue repair, where they assume trophic functions by removing debris and orchestrating the recruitment and activity of other cell types participating in tissue remodeling. They also antagonize M1 macrophage responses, which may be crucial for the activation of the wound healing response and for tissue homeostasis to be restored.

M2 macrophages also produce growth factors that stimulate epithelial cells and fibroblasts, including transforming growth factor-β1 (TGFβ1) and PDGF. Macrophage-derived TGFβ1 contributes to tissue regeneration and wound repair by promoting fibroblast differentiation into myofibroblasts, by enhancing expression of tissue inhibitors of metalloproteinases (TIMPs) that block the degradation of extracellular matrix (ECM) and by directly stimulating the synthesis of interstitial fibrillar collagens in myofibroblasts. Macrophage-derived PDGF also stimulates the proliferation of activated ECM-producing myofibroblasts.

M2 macrophages can also regulate wound healing independently of their interactions with myofibroblasts. Indeed, they produce matrix metalloproteinases (MMPs) and TIMPs that control ECM turnover, they engulf and digest dead cells, debris and various ECM components that would promote tissue-damaging M1 macrophage responses, and they secrete specific chemokines that recruit fibroblasts, TH2 cells and regulatory T (TReg) cells. Moreover, M2 macrophages produce factors that induce myofibroblast apoptosis, serve as antigen-presenting cells (APCs) that propagate antigen-specific TH2 and TReg cell responses (which promote wound healing while limiting the development of fibrosis) and express immunoregulatory proteins (such as IL-10, resistin-like molecule-α (RELMα; also known as RETNLα or FIZZ1), chitinase-like proteins and arginase 1 (ARG1)) that have been shown to decrease the magnitude and duration of inflammatory responses and promote wound healing.

M2 macrophages have been found to regulate important metabolic functions. These macrophages are induced by peroxisome proliferator activated receptor-γ (PPARγ) signaling and maintain adipocyte function, insulin sensitivity and glucose tolerance, which can prevent the development of diet-induced obesity and type 2 diabetes. It has been shown that IL-4-producing eosinophils are required to maintain M2 macrophages in healthy non-obese mice. Therefore, as obesity progresses, adipose tissue-associated macrophages switch from an M2-like phenotype to a classically activated M1-like phenotype with potent pro-inflammatory activity, with the NLRP3 inflammasome serving as the molecular switch by sensing obesity-associated danger signals.

Methods of reducing the expression of proinflammatory mediators, tumor necrosis factor-α, interleukin-6, and interleukin-1β are provided. The methods can include administering to a subject an effective amount of a composition including a curcumin analog to reduce the expression of proinflammatory mediators, tumor necrosis factor-α, interleukin-6, and interleukin-1β in the subject. The methods typically reduce disruption of the blood-brain barrier and reduce the formation of vasogenic edema following intracerebral hemorrhage. In some embodiments, the methods increase neurological outcome scores after ICH.

Methods of decreasing glioma progression are also provided. The method typically include administering to a subject an effective amount of a composition including a curcumin analog to induce cell death in cancer cells which possess a mutated p53 gene.

Methods of activating the production of macrophages are also provided. The methods can include administering a subject an effective amount of a composition including a curcumin analog to activate the production of macrophages. The methods typically activate the production of M2 phenotype macrophages. In some embodiments, the methods induce the production of M2 phenotype macrophages from M1 phenotype. Typically, the pool of M1 macrophages decreases. In some embodiments, the curcumin analogs promote tissue regeneration. In some embodiments, the analogs promote wound healing, tissue remodeling, angiogenesis, and extracellular matrix (ECM) deposition. In some embodiments, the curcumin analogs can treat and/or prevent obesity and type 2 diabetes.

B. Methods of Treatment

Reducing the expression of proinflammatory mediators, tumor necrosis factor-α, interleukin-6, and interleukin-1β can be therapeutically targeted through either local or systemic delivery. In some embodiments, the compositions are administered systemically and targeted to a local site in the brain. In some embodiments, the composition is administered about 1, 2, 3, 4, 5, 6 hours post ICH. Disclosed herein are methods wherein the therapeutic effect includes a reduction in hematoma size. The reduction in hematoma size can be about 50%. Disclosed herein are methods wherein the therapeutic effect includes a reduction in the brain hemoglobin content. The reduction in brain hemoglobin content can be about 20%. There may also be a reduction in IL-6, a cytokine that is clinically correlated with hematoma expansion. The reduction in IL-6 can be about 0.5, 1.0, 1.5, 2.0, 2.5, 3.0, 3.5, or 4.0-fold. There may also be a reduction in proinflammatory mediators. In some embodiments, the brain water content can be significantly decreased by 4%. There may also be an increase in neurological score of about 2.3 points.

The curcumin analogs and compositions are also useful in subjects with tumors. The disclosed compositions can be used to treat any disease where uncontrolled cellular proliferation occurs such as cancers. A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/ glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Disclosed is a method of directing an analog to tumors, including administering to the subject, any of the curcumin analogs disclosed herein. In some embodiments, the compositions are administered systemically and targeted to a local cancer site in the subject. The subject can have one or more sites to be targeted, wherein the moiety is directed to one or more of the sites to be targeted. In some embodiments, the analog can be directed to tumor angiogenesis in the subject. The curcumin analogs can have a therapeutic effect on the cancer. For example, the size of the tumor can be reduced, or the growth of the tumor can be reduced, stopped, or reversed. Disclosed herein are methods wherein the therapeutic effect includes a decrease in glioblastoma multiforme progression. In some embodiments, the curcumin analogs induce cell death in glioma cancer cells which possess a mutated p53 gene. In some embodiments, the curcumin analogs decrease AP-1 activity. In some embodiments, the curcumin analogs reduce NFκB-DNA binding. In some embodiments, the analogs decrease NFκB activation in glioma cells.

EXAMPLES

Example 1

Curcumin Analogs and Anti-cancer Effects on Human Glioblastoma Cells

Methods

Cell Culture: Human U87 MG (WHO grade III) glioblastoma cells were cultured in Dulbecco's Modified Eagle Medium (DMEM) supplemented with 10% fetal bovine serum (FBS) and antibiotics at 37° C. and 5% $CO_2$. For cell death studies, cells were plated in 96-well tissue culture plates at 6×103 cells/well. Cells were treated with 5 µM, 10 µM, 20 µM, 30 µM, and 40 µM concentrations of each analogue dissolved in DMSO. As a control a vehicle of 2% DMSO in supplemented DMEM was used.

Cell Death Assays: Cellular viability was quantified by the MTT (3-[4,5-dimethylthiazol-2-yl]-2,5-diphenyltetrazolium bromide) reduction assay.

Results

FIGS. 1A-1N shows the effect of the curcumin analogues on glioma cell viability. Of the 44 viable analogues tested, 14 showed significantly decreased cell viability in comparison to the Curcumin parent molecule. Data were compared by one-tailed Student's t-test (* $p<0.05$,  $p<0.01$, * $p<0.001$).

Of the 66 synthesized curcumin analogues, 44 were found to be more soluble than the parent compound.

In vitro testing of the curcumin analogs on human glioblastoma cells revealed that analogues 4, 11, 12, 16, 17, 23, 25, 29, 32, 36, 50, 54, 59, 65 all significantly outperformed curcumin in reducing cell viability (FIGS. 1A-1N). Notably, 10 of these analogues contain a methyl ether functional moiety.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A compound having the structure:

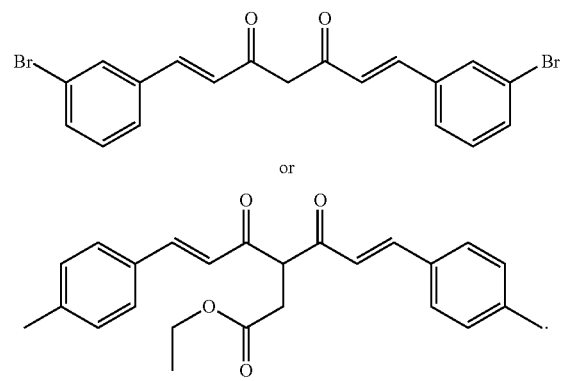

2. A pharmaceutical composition comprising one or more of the compounds, pharmaceutically acceptable salt, prodrug, clathrate, tautomer or solvate thereof according to claim 1 and a pharmaceutically acceptable excipient.

3. The composition of claim 2, wherein the one or more compounds are present in an effective amount to reduce the expression of proinflammatory mediators, tumor necrosis factor-α, interleukin-6, or interleukin-1β.

4. The composition of claim 2, wherein the one or more compounds are present in an effective amount to reduce disruption of the blood-brain barrier.

5. The composition of claim 2, wherein the one or more compounds are present in an effective amount to increase neurological outcome scores after intracerebral hemorrhage.

6. The composition of claim 2, wherein the one or more compounds are present in an effective amount to activate the production of M2 phenotype macrophages.

7. The composition of claim 2, wherein the one or more compounds are present in an effective amount to reduce NF-κB activity.

8. The composition of claim 2, wherein the one or more compounds are present in an effective amount to reduce AP-1 activity.

9. The composition of claim 2, wherein the one or more compounds are present in an effective amount to prevent and/or treat cancer.

10. The composition of claim 2, wherein the one or more compounds are present in an effective amount to prevent and/or treat malignant glioma.

11. The composition of claim 2, wherein the one or more compounds are present in an effective amount to induce, augment, or enhance an immune response against a disease or condition associated with microbial products, damaged cells, or activated lymphocytes.

12. The composition of claim 2, wherein the one or more compounds are present in an effective amount to treat or prevent atherosclerotic plaque, a fibrotic condition, inflammation, sarcoidosis, or multiple sclerosis.

13. The composition of claim 2, wherein the one or more compounds are present in an effective amount to treat or prevent pulmonary fibrosis or systematic sclerosis.

14. The composition of claim 2, wherein the one or more compounds are present in an effective amount to promote tissue regeneration.

15. The composition of claim 2, wherein the one or more compounds are present in an effective amount to promote parasite containment.

* * * * *